(12) United States Patent
Burke

(10) Patent No.: US 9,656,010 B2
(45) Date of Patent: May 23, 2017

(54) CONTROLLING IMPLANTED BLOOD PUMPS

(71) Applicant: Thoratec Corporation, Pleasanton, CA (US)

(72) Inventor: David J. Burke, Concord, MA (US)

(73) Assignee: TC1 LLC, St. Paul, MN (US)

( * ) Notice: Subject to any disclaimer, the term of this patent is extended or adjusted under 35 U.S.C. 154(b) by 53 days.

(21) Appl. No.: 14/223,029

(22) Filed: Mar. 24, 2014

(65) Prior Publication Data

US 2014/0324165 A1 Oct. 30, 2014

Related U.S. Application Data

(63) Continuation of application No. 13/188,510, filed on Jul. 22, 2011, now Pat. No. 8,721,719.

(Continued)

(51) Int. Cl.
*A61M 1/10* (2006.01)
*G06F 19/00* (2011.01)
*A61M 1/12* (2006.01)

(52) U.S. Cl.
CPC .......... *A61M 1/1086* (2013.01); *A61M 1/122* (2014.02); *G06F 19/3406* (2013.01);
(Continued)

(58) Field of Classification Search
CPC .............................. A61M 1/1086; A61M 1/10
(Continued)

(56) References Cited

U.S. PATENT DOCUMENTS 5,279,292 A 1/1994 Baumann et al.
5,383,840 A 1/1995 Heilman et al.
(Continued)

FOREIGN PATENT DOCUMENTS

WO WO 03/072160 A2 9/2003
WO WO 2007/053881 A1 5/2007
(Continued)

OTHER PUBLICATIONS

Endo G. et al., "Control strategy for biventricular assistance with mixed-flow pumps," [online], [retrieved on Apr. 7, 2010]. Retrieved from the Internet: http://www.ncbi.nlm.nih.gov/pubmed/10971243, 1 page.

(Continued)

*Primary Examiner* — Matthew Schall
(74) *Attorney, Agent, or Firm* — Kilpatrick Townsend & Stockton LLP

(57) ABSTRACT

A blood pump controller includes a microcontroller and a communication interface. The microcontroller is configured to communicate with various types of blood pump communication modules. The microcontroller is further configured to determine, based on communication with a particular type of blood pump communication module, the particular type of blood pump communication module communicated with. The microcontroller is further configured to select, based on the determination of the particular type of blood pump communication module, control logic used to control the particular type of blood pump communication module. The microcontroller is further configured to generate, based on the selected control logic, commands for controlling the blood pump communication module. The communication interface is configured to connect the microcontroller to the particular type of blood pump communication module.

19 Claims, 7 Drawing Sheets

Related U.S. Application Data

(60) Provisional application No. 61/366,757, filed on Jul. 22, 2010.

(52) U.S. Cl.
CPC ......... *A61M 1/101* (2013.01); *A61M 2205/17* (2013.01); *A61M 2205/3515* (2013.01); *A61M 2205/3561* (2013.01); *A61M 2205/6018* (2013.01); *A61M 2205/8206* (2013.01)

(58) Field of Classification Search
USPC ............................................. 623/3.13, 3.27
See application file for complete search history.

(56) References Cited

U.S. PATENT DOCUMENTS

| | | | |
|---|---|---|---|
| 5,569,156 A | 10/1996 | Mussivand | |
| 5,704,891 A | 1/1998 | Mussivand | |
| 5,725,357 A | 3/1998 | Nakazeki et al. | |
| 5,733,313 A | 3/1998 | Barreras, Sr. et al. | |
| 5,766,207 A | 6/1998 | Potter et al. | |
| 5,947,703 A | 9/1999 | Nojiri et al. | |
| 6,067,474 A | 5/2000 | Schulman et al. | |
| 6,123,726 A | 9/2000 | Mori et al. | |
| 6,146,325 A | 11/2000 | Lewis et al. | |
| 6,234,772 B1 | 5/2001 | Wampler et al. | |
| 6,264,635 B1 | 7/2001 | Wampler et al. | |
| 6,269,266 B1 | 7/2001 | Leysieffer | |
| 6,468,041 B2 | 10/2002 | Ozaki | |
| 6,498,951 B1 | 12/2002 | Larson et al. | |
| 6,575,717 B2 | 6/2003 | Ozaki et al. | |
| 6,589,030 B2 | 7/2003 | Ozaki | |
| 6,605,032 B2 | 8/2003 | Benkowski et al. | |
| 6,626,644 B2 | 9/2003 | Ozaki | |
| 6,632,169 B2 | 10/2003 | Korakianitis et al. | |
| 6,652,447 B2 | 11/2003 | Benkowski et al. | |
| 6,688,861 B2 | 2/2004 | Wampler | |
| 6,707,200 B2 | 3/2004 | Carroll et al. | |
| 6,817,836 B2 | 11/2004 | Nose et al. | |
| 6,949,066 B2 | 9/2005 | Bearnson et al. | |
| 7,138,776 B1 | 11/2006 | Gauthier et al. | |
| 7,150,711 B2 | 12/2006 | Nüsser et al. | |
| 7,229,474 B2 | 6/2007 | Hoffmann et al. | |
| 7,239,098 B2 | 7/2007 | Masino | |
| 7,284,956 B2 | 10/2007 | Nose et al. | |
| 7,462,019 B1 | 12/2008 | Allarie et al. | |
| 7,497,116 B2 | 3/2009 | Miyakoshi et al. | |
| 7,511,443 B2 | 3/2009 | Townsend et al. | |
| 7,591,777 B2 | 9/2009 | LaRose et al. | |
| 7,645,225 B2 | 1/2010 | Medvedev et al. | |
| 7,699,588 B2 | 4/2010 | Mendler | |
| 7,854,631 B2 | 12/2010 | Townsendl et al. | |
| 7,859,208 B2 | 12/2010 | Ayre et al. | |
| 7,861,582 B2 | 1/2011 | Miyakoshi et al. | |
| 7,887,479 B2 | 2/2011 | LaRose et al. | |
| 7,951,062 B2 | 5/2011 | Morello | |
| 7,976,271 B2 | 7/2011 | LaRose et al. | |
| 8,157,720 B2 | 4/2012 | Marseille et al. | |
| 8,303,482 B2 | 11/2012 | Schima et al. | |
| 8,382,830 B2 | 2/2013 | Maher et al. | |
| 8,388,384 B2 | 3/2013 | Cotter | |
| 8,394,009 B2 | 3/2013 | Bolyard et al. | |
| 8,506,470 B2 | 8/2013 | Larose et al. | |
| 8,517,699 B2 | 8/2013 | Horvath | |
| 8,556,795 B2 | 10/2013 | Bolyard et al. | |
| 8,562,508 B2 | 10/2013 | Dague et al. | |
| 8,585,571 B2 | 11/2013 | Bachman et al. | |
| 8,597,350 B2 | 12/2013 | Rudser et al. | |
| 8,721,719 B2 | 5/2014 | Burke | |
| 8,753,256 B2 | 6/2014 | Bolyard et al. | |
| 8,764,621 B2 | 7/2014 | Badstibner et al. | |
| 8,870,739 B2 | 10/2014 | Larose et al. | |
| 8,882,477 B2 | 11/2014 | Fritz, IV et al. | |
| 8,956,275 B2 | 2/2015 | Bolyard et al. | |
| 2005/0071001 A1 | 3/2005 | Jarvik | |
| 2005/0187594 A1 | 8/2005 | Hatlestad | |
| 2009/0149950 A1 | 6/2009 | Wampler | |
| 2010/0130809 A1 | 5/2010 | Morello | |
| 2010/0241223 A1* | 9/2010 | Lee ........................ A61M 1/127 623/3.27 |
| 2010/0305692 A1 | 12/2010 | Thomas et al. | |
| 2010/0327687 A1 | 12/2010 | Iannello et al. | |
| 2011/0071337 A1 | 3/2011 | Thompson et al. | |
| 2011/0160516 A1* | 6/2011 | Dague ..................... A61M 1/12 600/16 |
| 2011/0218383 A1 | 9/2011 | Broen et al. | |
| 2011/0237863 A1 | 9/2011 | Ricci et al. | |
| 2011/0313237 A1 | 12/2011 | Miyakoshi et al. | |
| 2012/0157754 A1 | 6/2012 | D'Amrosio | |
| 2012/0226097 A1 | 9/2012 | Smith et al. | |
| 2012/0245681 A1 | 9/2012 | Casas et al. | |
| 2013/0225911 A1 | 8/2013 | Bolyard et al. | |
| 2013/0310631 A1 | 11/2013 | Lee et al. | |
| 2013/0314047 A1 | 11/2013 | Eagle et al. | |
| 2013/0331934 A1 | 12/2013 | Kabir et al. | |
| 2014/0005466 A1 | 1/2014 | Crosby et al. | |
| 2014/0066689 A1 | 3/2014 | Rainier et al. | |
| 2014/0073838 A1 | 3/2014 | Dague et al. | |
| 2014/0100413 A1 | 4/2014 | Casas et al. | |
| 2014/0194985 A1 | 7/2014 | Vadala, Jr. | |
| 2014/0275723 A1 | 9/2014 | Fritz, IV et al. | |
| 2014/0275757 A1 | 9/2014 | Goodwin et al. | |
| 2014/0303426 A1 | 10/2014 | Kerkhoffs et al. | |
| 2014/0357937 A1 | 12/2014 | Reyes et al. | |
| 2015/0051438 A1 | 2/2015 | Taskin | |

FOREIGN PATENT DOCUMENTS

| | | |
|---|---|---|
| WO | WO 2007/056592 A2 | 5/2007 |
| WO | WO 2009/109344 A1 | 9/2009 |
| WO | WO 2012/012552 A1 | 1/2012 |

OTHER PUBLICATIONS

Fukamachi et al., "Development of a Small Implantable Right Ventricular Assist Device," ASAIO Journal, 2005, pp. 730-735.

Motomura et al., "Ten-Year NEDO BVAD Development Program: Moving Forward to the Clinical Area," ASAIO Journal 2006, pp. 378-385.

Nose et al., "Development of a Totally Implantable Biventricular Bypass Centrifugal Blood Pump System," The Annals of Thoracic Surgery, Ann. Thorac. Surg., 1999;68:775-779.

Notification of Transmittal of the International Search Report and the Written Opinion of the International Searching Authority, or the Declaration and International Search Report and Written Opinion of the International Searching Authority for International Application No. PCT/US2011/044707 mailed on Oct. 31, 2011, 10 pages.

Pristas et al., "Protocol for Releasing Novacor Left Ventricular Assist System Patients Out-of-Hospital", ASAIO Journal 1995; 41:M539-M543, 5 pages.

Non-Final Office Action for U.S. Appl. No. 13/188,510 mailed on Oct. 12, 2012, 4 pages.

Notice of Allowance for U.S. Appl. No. 13/188,510 mailed on Dec. 24, 2013, 8 pages.

\* cited by examiner

CONTROLLING IMPLANTED BLOOD PUMPS

CROSS REFERENCE TO RELATED APPLICATIONS

The present application is a Continuation of U.S. Ser. No. 13/188,510 filed Jul. 22, 2011 (Allowed), which application claims the benefit under 35 USC 119(e) of U.S. Provisional Application No. 61/366,757 filed Jul. 22, 2010; the full disclosures of which are incorporated herein by reference in their entirety for all purposes.

TECHNICAL FIELD

This disclosure relates to controlling implanted blood pumps.

BACKGROUND

Blood pumps are used to augment or replace the pumping function of the left and/or right ventricles of the heart. For example, ventricular assistance may be provided by an implanted blood pump that is connected in parallel with a person's heart and is regulated by a controller. In the case of bi-ventricular assistance, two implantable blood pumps are used, each having its own dedicated controller.

SUMMARY

In bi-ventricular applications, rather than requiring a dedicated controller for each blood pump, a single, universal controller provides simultaneous and independent control of each blood pump. The controller controls the blood pumps without the need for, for example, two sets of cables and power management components, thereby reducing the patient's equipment maintenance burdens and costs.

To control blood pumps, such as one or two implanted ventricular assist devices (VADs), the universal controller communicates with the VADs through one or more communication modules. The controller is capable of controlling a single VAD in either a right VAD (RVAD) or left VAD (LVAD) configuration, and is capable of controlling two VADs in a bi-ventricular VAD (BiVAD) configuration. The controller provides a common user interface regardless of the type or number of VADs being controlled, thus providing a standardized look and feel for a user. As such, the controller provides a unitary device capable of controlling multiple types of blood pumps arranged in multiple configurations.

In a general aspect, a blood pump controller includes a microcontroller and a communication interface. The microcontroller is configured to communicate with various types of blood pump communication modules. The microcontroller is further configured to determine, based on communication with a particular type of blood pump communication module, the particular type of blood pump communication module communicated with. The microcontroller is further configured to select, based on the determination of the particular type of blood pump communication module, control logic used to control the particular type of blood pump communication module. The microcontroller is further configured to generate, based on the selected control logic, commands for controlling the blood pump communication module. The communication interface is configured to connect the microcontroller to the particular type of blood pump communication module.

Implementations may include one or more of the following features. For example, two or more blood pumps are connected to the blood pump communication module. Furthermore, the control logic calculates, based on status and configuration information received from the blood pump communication module, speeds for the two or more blood pumps. The microcontroller is further configured to receive status and configuration information from the blood pump communication module. The blood pump controller includes a system display module configured to display a subset of the status and configuration information received from the blood pump communication module. The blood pump controller further includes a network interface module configured to output patient data to a patient monitoring device, and includes a reference signal module configured to generate time based signals and precision voltages that are utilized in fault detection.

In another aspect, a system includes two or more blood pumps and a blood pump communication module connected to the two or more blood pumps. The system also includes a blood pump controller connected to the blood pump communication module that includes a microcontroller. The microcontroller is configured to communicate with various types of blood pump communication modules. The microcontroller is further configured to determine, based on communication with a particular type of blood pump communication module, the particular type of blood pump communication module communicated with. The microcontroller is further configured to select, based on the determination of the particular type of blood pump communication module, control logic used to control the particular type of blood pump communication module. The microcontroller is further configured to generate, based on the selected control logic, commands for controlling the blood pump communication module. The communication interface is configured to connect the microcontroller to the particular type of blood pump communication module.

In some implementations, the blood pump communication module is configured to connect to two axial flow blood pumps. The blood pump communication module includes a first blood pump microcontroller configured to monitor flow information in a first of the axial flow blood pumps, and generate, based on the generated commands, signals to energize coils in the first of the axial flow blood pumps in a sequence necessary to operate the first of the axial flow blood pumps at a specific speed. Additionally, the blood pump communication module includes a second blood pump microcontroller configured to monitor flow information in a second of the axial flow blood pumps, and generate, based on the generated commands, signals to energize coils in the second of the axial flow blood pumps in a sequence necessary to operate the second of the axial flow blood pumps at a specific speed.

In some implementations, the blood pump communication module further includes a backup microcontroller configured to monitor the operational states of the first blood pump microcontroller and the second blood pump microcontroller, and, when either the first blood pump microcontroller or the second blood pump microcontroller fails, assume operations of the failed blood pump microcontroller. The blood pump communication module also includes a universal connector configured to connect the first blood pump microcontroller to the first of the axial flow blood pumps and connect the second blood pump microcontroller to the second of the axial flow blood pumps.

In some implementations, the first blood pump microcontroller is configured to determine if a blood pump is connected to the universal connector to determine, when a blood pump is determined to be connected to the universal connector, a type of the blood pump that is connected to the universal connector, and to send, to the microcontroller, the type of the blood pump that is connected to the universal connector. In some implementations, the first blood pump microcontroller is configured to determine if the type of the blood pump that is connected to the universal connector is a type of blood pump that is supported by the blood pump communication module, and to send the generated commands to the blood pump communication module when the blood pump that is connected to the universal connector is a type of blood pump that is supported by the blood pump communication module.

In some implementations, the blood pump communication module is configured to connect to two centrifugal flow blood pumps. The blood pump communication module includes a first blood pump communication interface configured to monitor flow information in a first of the centrifugal flow blood pumps, buffer a first portion of the generated commands, and communicate the first portion of the generated commands to the first of the centrifugal flow blood pumps. Additionally, the blood pump communication module includes a second blood pump communication interface configured to monitor flow information in a second of the centrifugal flow blood pumps, buffer a second portion of the generated commands, and communicate the second portion of the generated commands to the second of the centrifugal flow blood pumps. In some embodiments, the blood pump communication module includes a universal connector configured to connect the first blood pump communication interface to the first of the centrifugal flow blood pumps and connect the second blood pump communication interface to the second of the centrifugal flow blood pumps.

In some implementations, the blood pump communication module is configured to connect to a axial flow blood pump and a centrifugal flow blood pump. The blood pump communication module includes a blood pump microcontroller configured to monitor flow information in the axial flow blood pump, and generate, based on a first portion of the generated commands, signals to energize coils in the axial flow blood pump in a sequence necessary to operate the axial flow blood pump at a particular speed. Additionally, the blood pump communication module includes a backup microcontroller configured to monitor the operational state of the blood pump microcontroller, and, when the blood pump microcontroller fails, assume operation of the blood pump microcontroller. Furthermore, the blood pump communication module includes a blood pump communication interface configured to monitor flow information in the centrifugal flow blood pump, buffer a second portion of the generated commands, and communicate the second portion of the generated commands to the centrifugal flow blood pump. Additionally, the blood pump communication module includes a universal connector configured to connect the blood pump microcontroller to the axial flow blood pump and connect the blood pump communication interface to the centrifugal flow blood pump.

In another general aspect, a method includes communicating with various types of blood pump communication modules, and determining, based on the communication with a particular type of blood pump communication module, the particular type of blood pump communication module communicated with. The method further includes selecting, based on the determination of the particular type of blood pump communication module, control logic to control the particular type of blood pump communication module. The method further includes generating, based on the selected control logic, commands for controlling the blood pump communication module.

The details of one or more implementations are set forth in the accompanying drawings and the description below. Other features, objects, and advantages will be apparent from the description and drawings, and from the claims.

DETAILED DESCRIPTION

Figure 1:
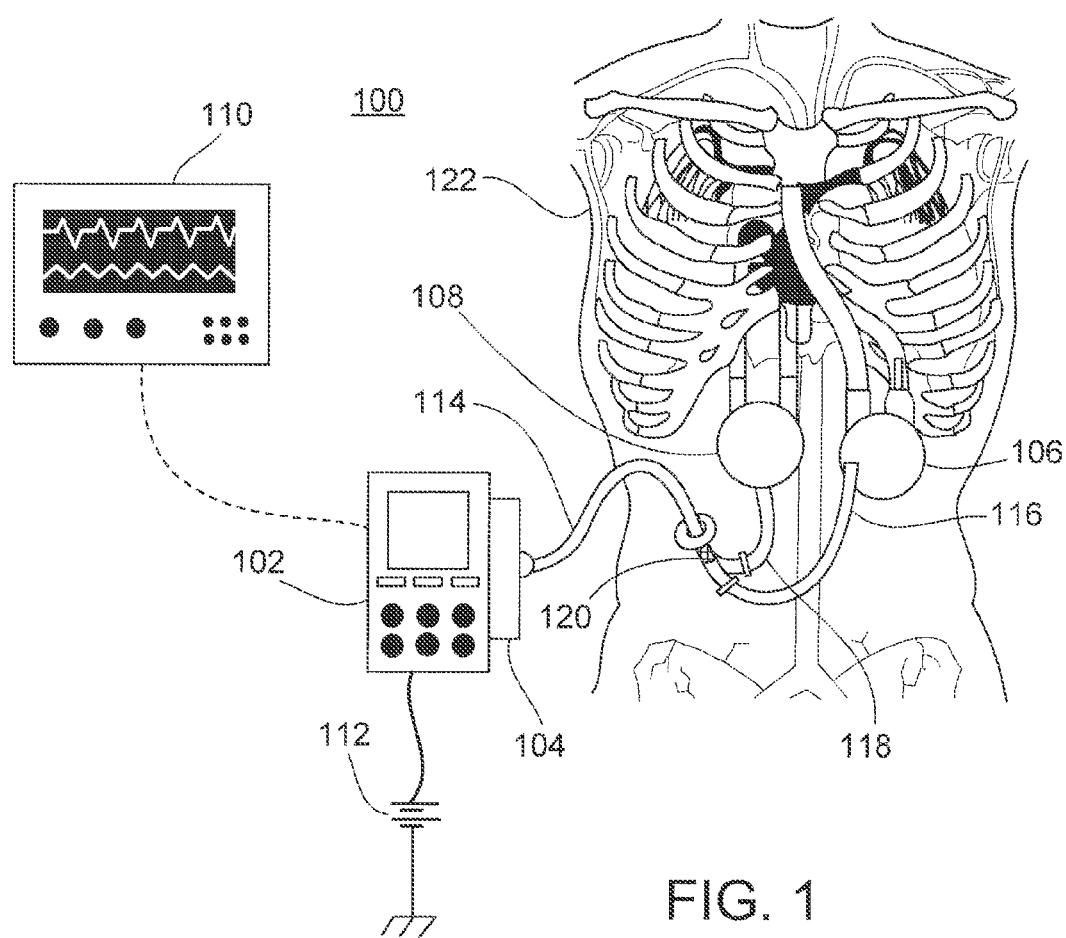
FIG. 1 illustrates an example of a ventricular assist system including a universal blood pump controller and blood pump communication module.

Referring to FIG. 1, a ventricular assist system 100 includes a blood pump controller 102 connected to a medical monitor 110 and to a blood pump communication module 104. The blood pump controller 102 includes, among other things, a microcontroller for generating control signals to control the blood pump communication module 104 and a communication interface for connecting the blood pump controller 102 to the blood pump communication module 104, as will be discussed in greater detail below. The communication module 104 is connected to one or more blood pumps 106, 108 (e.g., VADs) via a cable 114 of the communication module 104 and a set of cables 116, 118 connected to the pumps 106, 108, respectively. The cable 114 passes through the skin of a patient, and the set of pump cables 116, 118 is connected to the cable 114 via a connector 120 implanted in the patient's body 122. An exemplary cable 114 and connector 120 for use in conjunction with the controller 102 and blood pump communication module 104 are described in U.S. patent application Ser. No. 13/155,009, filed Jun. 7, 2011, which is incorporated herein by reference in its entirety. Alternatively, the communication module 104 may wirelessly communicate with one or more blood pumps 106, 108.

The blood pump communication module 104 and the blood pump controller 102 can be connected to, and configured to control, multiple types of blood pumps 106, 108 in multiple configurations (e.g., one or more axial flow VADs, one or more centrifugal flow VADs, or an axial flow VAD and a centrifugal flow VAD). As discussed in more detail below, the configuration of the blood pump communication module 104 determines and/or detects the type(s) of blood pump(s) to which the blood pump communication module 104 is connected, and based on this determination, the blood pump controller 102 sends appropriate control and data signals to each blood pump via the blood pump communication module 104.

To provide control over a number of different types and configurations of blood pumps, a single blood pump controller 102 can be connected to any of a number of types of blood pump communication modules 104. For example, if the blood pump communication module 104 takes the form of a peripheral unit as shown in FIG. 1 that includes a communication port (not shown), the communication port of the blood pump communication module 104 can be directly connected to a corresponding port (not shown) of the blood pump controller 102, such that the blood pump communication module 104 is releasably connected to the blood pump controller 102 (FIG. 1). Alternately, the blood pump communication module 104 can be indirectly connected to a corresponding communication port (not shown) of the blood pump controller 102 through, for example, a cable or the use of wireless communication. Alternatively, the blood pump communication module 104 can take the form of a PC card or other card-type form factor that can be inserted into a slot (not shown) of the blood pump controller 102, or the blood pump communication module 104 can take the form of a daughterboard or mezzanine board (not shown) that is installed in the blood pump controller 102 during or after manufacture of the blood pump controller 102. In any of these configurations, the blood pump controller 102 can be connected to any of the varying types of blood pump communication modules 104 in order to provide control over the varying types of implanted blood pumps 106, 108 as will be described below. In this manner, the design of the blood pump controller provides a high degree of modularity to the ventricular assist system.

The blood pump controller 102 is configured to communicate and interface with either a proprietary system monitor device or a standard medical or physiological monitor unit employed, for example, in a hospital or other health care facility, including but not limited to a tablet computer. The blood pump controller 102 is connected to the medical monitor 110 through either a wired (e.g., through one or more serial or parallel communication ports) or wireless (e.g., utilizing IEEE 802.11, Bluetooth, or Infrared Data Association hardware and standards) configuration. Furthermore, the blood pump controller 102 is connected to an external power source 112 that is capable of powering one or more of the blood pump controller 102, the blood pump communication module 104, and the blood pumps 106, 108.

Figure 2A:
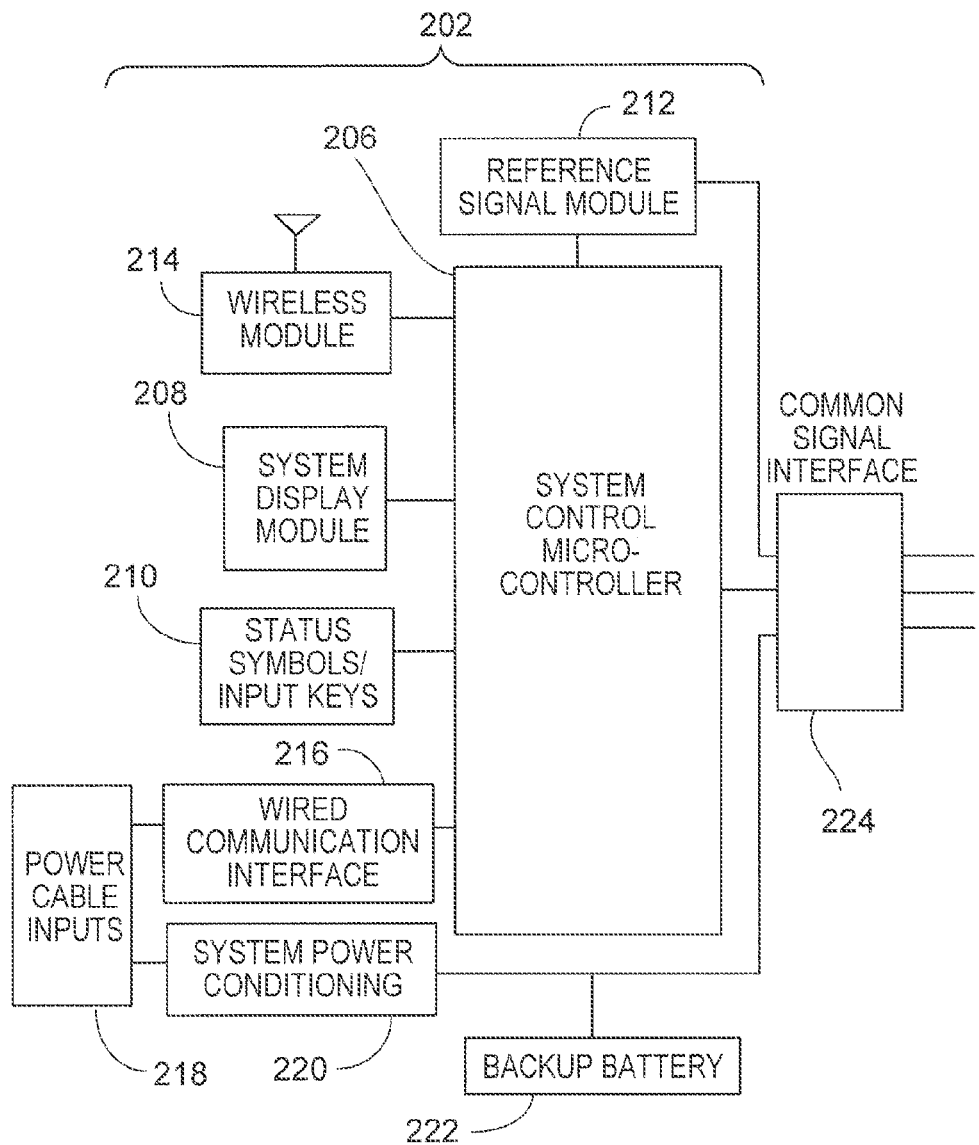
FIGS. 2A-2B are schematic representations of a universal rotary blood pump controller and a rotary blood pump communication module configured to communicate with two axial flow rotary blood pumps.
Figure 2B:
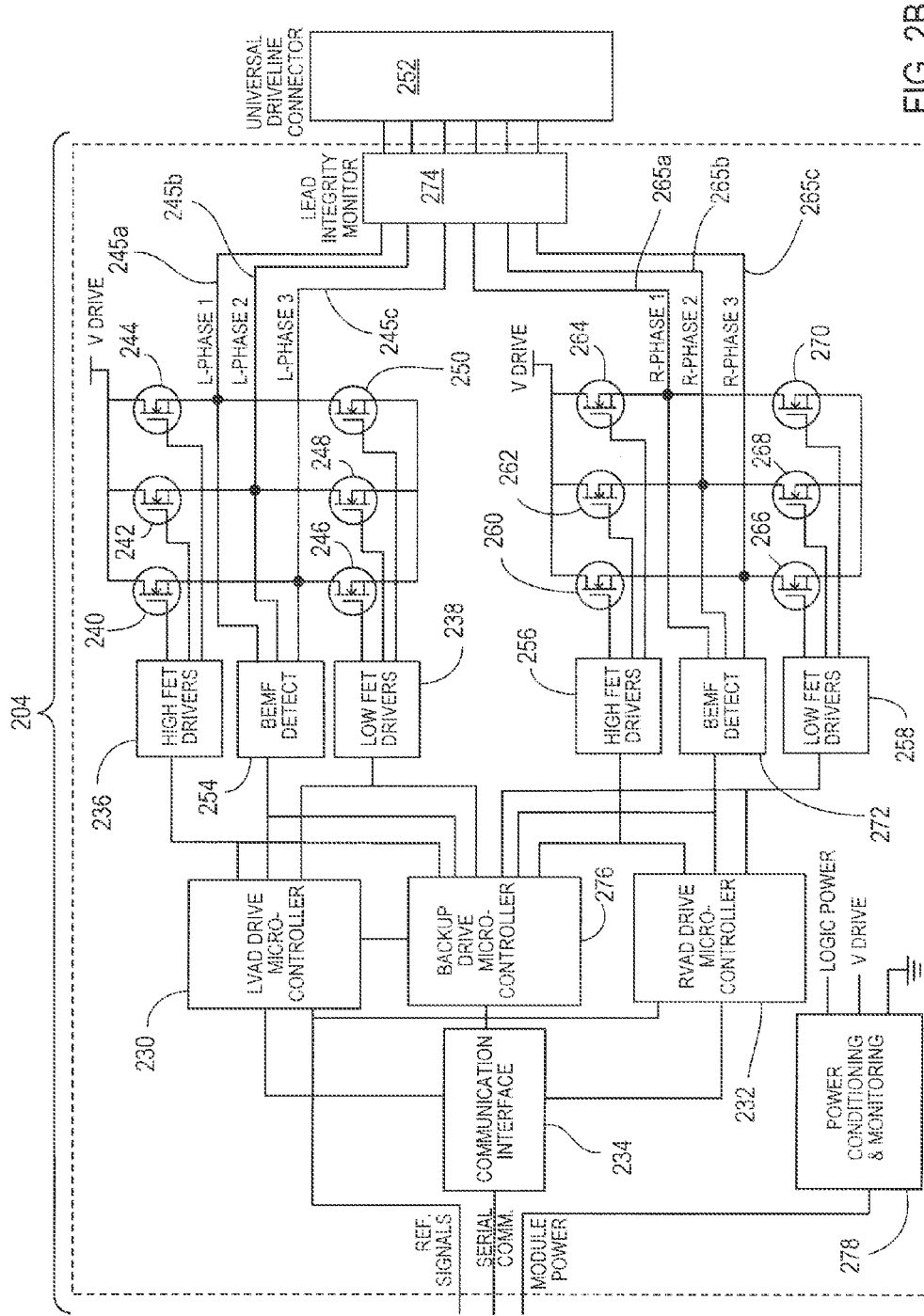
Figure 3:
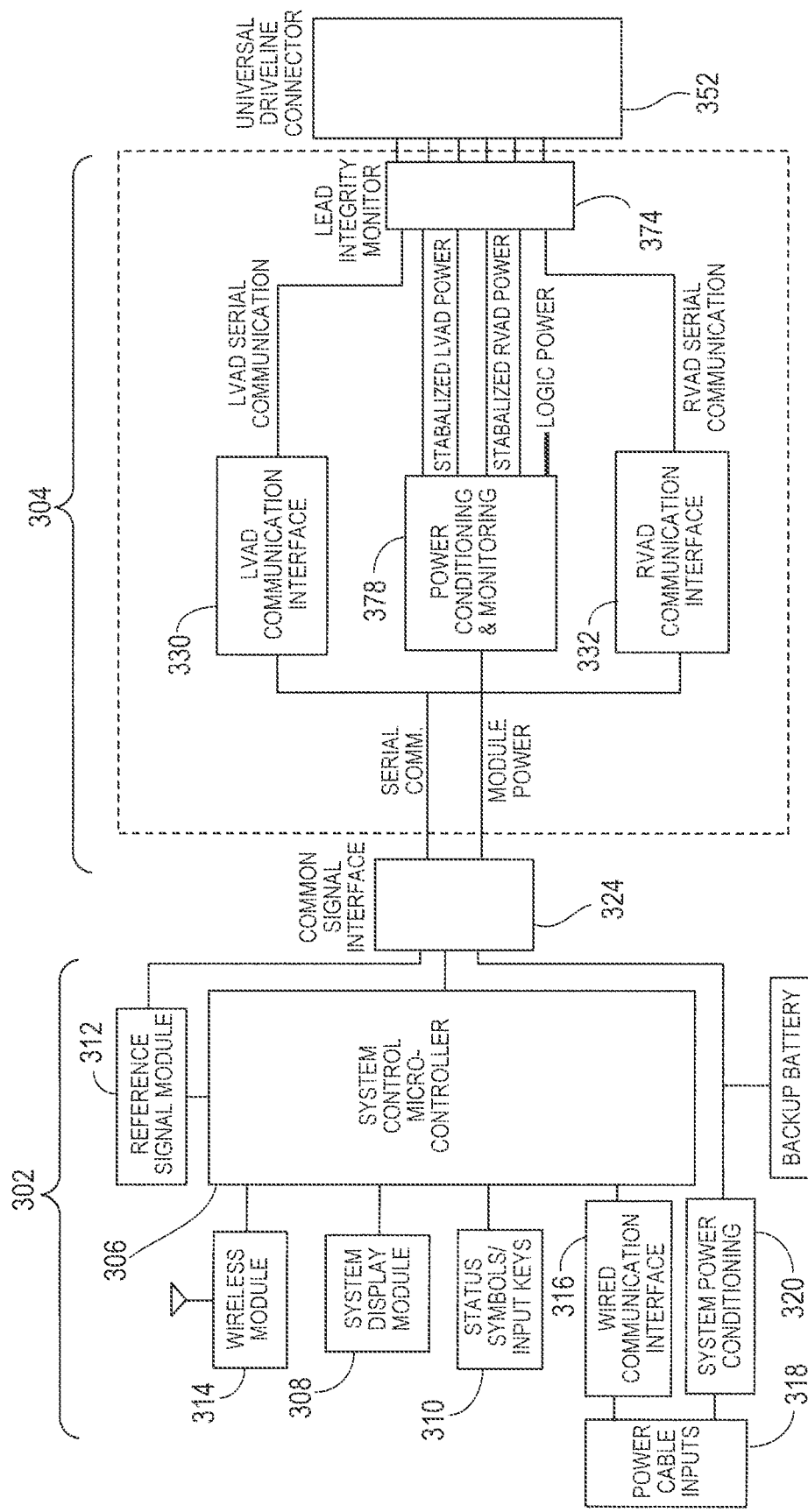
FIG. 3 is schematic representation of a universal rotary blood pump controller and a rotary blood pump communication module configured to communicate with two centrifugal flow rotary blood pumps.

Various exemplary implementations of the blood pump controller 102 and the blood pump communication module 104 are illustrated in FIGS. 2-4. In each of these implementations, the blood pump controller 102 can be connected to the blood pump communication module 104 in the various manners described above.

FIGS. 2A-2B illustrate a blood pump controller 202 connected to a blood pump communication module 204 that supports one or more blood pumps 106, 108, such as one or more axial flow VADs. The blood pump controller 202 includes a microcontroller 206. The microcontroller 206 provides the primary control for the blood pump controller 202. The microcontroller 206 can, for example, take the form of one or more processors coupled to one or more storage devices (not shown), where the one or more storage devices store one or more programs or other instructions for execution by the one or more processors. Alternatively, the microcontroller 206 can, for example, take the form of a field-programmable gate array (FPGA) being programmed with one or more programs or other instructions.

The microcontroller 206 includes one or more programs that are utilized depending on the configuration of the blood pump communication module 204 to which the blood pump controller 202 is connected. For example, the microcontroller 206 can execute a utilized program to, among other things, produce commands for operating the blood pump communication module 204 and through it one or more VADs connected to the blood pump communication module 204. For example, the microcontroller 206 can send control outputs to the blood pump communication module 204 indicating one or more speed(s) at which the one or more VADs should operate. Alternatively or additionally, the microcontroller 206 can send control outputs to the blood pump communication module 204 to request power and flow measurements for the one or more VADs, request information regarding an actual blood pump speed, or request operational/fault status for each blood pump control channel. The different programs stored may include control modes based on pulsatility index, pulse (artificial pulse), continuous flow or a combination. In practice, the microcontroller can be designed to implement any one or a combination of these control programs indefinitely, for a fixed duration, and at periodic intervals. For instance, a particular control mode (e.g., pulse mode) may be considered to be beneficial for a patient immediately post operation, while a continuous mode may be considered appropriate for a patient during recovery. Or, to transition the patient between post operation and recovery, both programs can be implemented alternately for a period of time.

The blood pump controller 202 further includes a system display module 208 connected to the microcontroller 206. The system display module 208 includes, for example, a liquid crystal display (LCD) that is used to display various information regarding the operation of the blood pump controller 202 and the blood pump communication module 204 supplied by the microcontroller 206.

The blood pump controller 202 can also include status symbols and input keys 210. The status symbols 210 can include, for example, illuminated indicators that resemble a red heart for indication of the operational state of one or more VADs connected to the blood pump communication module 204; one or more power indicator(s) for indication of the power level(s) in the one or more batteries used to power the pump and/or the blood pump controller 202; and a yellow wrench for indicating that the blood pump controller 202, the blood pump communication module 204, or the one or more VADs connected to the blood pump communication module 204 is in need or service or repair. The input keys 210 receive input associated with various commands regarding the operation of the blood pump controller 202, the blood pump communication module 204, or the one or more VADs connected to the blood pump communication module 204. The blood pump controller 202 can be configured to have only one fixed operational speed for the pump, or the blood pump controller 202 can be preset with a number of different speed profiles from which a user can select, or the blood pump controller 202 can have a preset minimum speed and a preset maximum speed and a user, via the input keys 210, can set a speed at which the one or more VADs connected to the blood pump communication module 204 are to operate within the predefined speed range.

The blood pump controller 202 also includes a reference signal module 212 connected to the microcontroller 206. The reference signal module 212 facilitates integrity checks of the various components of the blood pump controller 202 and the blood pump communication module 204. In order to facilitate such integrity checks, the reference signal module 212 produces one or more precision time-based signals and precision interlocked voltages. The reference signal module 212 supplies the precision time-based signals and precision interlocked voltages to the microcontroller 206 for comparison with various signals and voltages output by the components of the blood pump controller 202 and the blood pump communication module 204. Alternatively, the reference signal module 212 can itself compare the precision time-based signals and precision interlocked voltages with the various signals and voltages output by the components of the blood pump controller 202 and the blood pump communication module 204 and output the results of the comparison to the microcontroller 206.

Based on the comparison between the precision time-based signals and precision interlocked voltages and the various signals and voltages output by the components of the blood pump controller 202 and the blood pump communication module 204, the microcontroller 206 determines if a fault is present regarding one or more of the components of the blood pump controller 202 and the blood pump communication module 204. When a fault is determined, the microcontroller 206 outputs information regarding the fault for display on the display module 208 or through the status symbols 210. Alternatively or additionally, when a fault is determined, the microcontroller 206 alters outputs to the blood pump communication module 204 or it can cease providing outputs to the blood pump communication module 204.

The blood pump controller 202 further includes a wireless communication module 214 connected to the microcontroller 206. The wireless communication module 214 utilizes one or more known wireless communication protocols and their associated hardware, as appropriate for transfer of medical information. For example, the wireless communication module 214 can be configured to utilize one or more of IEEE 802.11, Bluetooth, or Infrared Data Association (IrDA) hardware and wireless standards that are known to those with ordinary skills in the art. The microcontroller 206 utilizes the wireless communication module 214 to communicate with, for example, an external medical monitor, providing the external medical monitor with various information regarding the operating states of the blood pump controller 202, the blood pump communication module 204, or one or more VADs connected to the blood pump communication module 204, or various information regarding the patient within whom the one or more VADs are implanted.

The blood pump controller 202 further includes a wired communication module 216 connected to the micro controller 206. The wired communication module 216 utilizes one or more known wired communication protocols and their associated hardware. For example, the wired communication module 216 utilizes one or more of serial, parallel, or universal serial bus (USB) hardware and standards. The wired communication module 216 operates similarly to the wireless communication module 214 described above. In particular, the microcontroller 206 utilizes the wired communication module 216 to communicate with an external medical monitor, providing the external medical monitor with various information regarding the operating states of the blood pump controller 202, the blood pump communication module 204, or one or more VADs connected to the blood pump communication module 204, or various information regarding the patient within whom the one or more VADs are implanted.

The blood pump controller 202 further includes power cable inputs 218 connected to the wired communication interface 216 and a system power conditioning module 220. The power cable inputs 218 provide the external connection points for both the wired communication interface 216 and the system power conditioning module 220 for connection to an external power source. The power cable inputs 218 can take the form of ports through which various independent cables are attached or can take the form of cables integrated into the structure of the blood pump controller 202.

The system power conditioning module 220 connects to the external power source and conditions the power supplied by the external power source for use in charging a battery 222 included in the blood pump controller 202, and in powering the components of the blood pump communication module 204. The battery 222 takes the form of a backup power unit for powering both the blood pump controller 202 and the blood pump communication module 204 in a situation where power from the external power source is interrupted.

The blood pump controller 202 further includes a common signal interface 224 connected to the microcontroller 206 and through which the blood pump controller 202 communicates with the blood pump communication module 204. Depending on the configuration of the blood pump controller 202 and the blood pump communication module 204, the common signal interface 224 can take different forms and be located in different places on the blood pump controller 202. For example, if the blood pump communication module 204 takes the form of a PC card or other card-type form factor, the common signal interface 224 is located internal to a slot (not shown) on the blood pump controller 202 and into which the blood pump communication module 204 is inserted. Alternatively, if the blood pump communication module 204 takes the form of a daughter-board or mezzanine board (not shown) that is installed internal to the blood pump controller 202, the common signal interface 224 can be located internal to the blood pump controller 202 on, for example, a motherboard containing one or more of the components of the blood pump controller 202. Alternatively, if the blood pump communication module 204 takes the form of an external peripheral unit (not shown), the common signal interface 224 can be located on an external surface of the blood pump controller 202 allowing for easy and quick connection and disconnection of the blood pump communication module 204.

Referring to FIGS. 2A and 2B, the blood pump communication module 204 includes a LVAD microcontroller 230 and a RVAD microcontroller 232. Based on the commands produced by the microcontroller 206 for operating the blood pump communication module 204, the LVAD microcontroller 230 generates and outputs signals necessary to operate, for example, an axial flow VAD configured to assist the left ventricle. Likewise, based on the commands produced by the microcontroller 206 for operating the blood pump communication module 204, the RVAD microcontroller 232 generates and outputs signals necessary to operate, for example, an axial flow VAD configured to assist the right ventricle.

The blood pump communication module 204 further includes a communication interface 234 connected to the common signal interface 224 and to each of the LVAD microcontroller 230 and the RVAD microcontroller 232. The blood pump communication module 204 operates as a splitter such that control outputs from the microcontroller 206 are received at each of the LVAD microcontroller 230 and the RVAD microcontroller 232. Alternatively, the blood pump communication module 204 parses the control outputs from the microcontroller 206 and routes the control outputs to the appropriate one of the LVAD microcontroller 230 and the RVAD microcontroller 232 depending upon for which of the LVAD microcontroller 230 and the RVAD microcontroller 232 the control outputs are intended.

The LVAD microcontroller 230 is connected to a high field effect transistor (FET) driver 236 and a low FET driver 238. The high FET driver 236 and low FET driver 238 are connected to multiple FETs 240-250. Based in part on the control outputs from the microcontroller 206, the LVAD microcontroller 230 can control the high FET driver 236 and low FET driver 238 to supply control voltages to FETs 240-250. In this manner, the FETs 240-250 can act as switches for alternately supplying a driving voltage and a ground to each of three left phases leads 245a, b, c. The three left phase leads 245a, b, c are connected through a universal driveline connector 252 to, for example, an axial flow VAD. The universal driveline connector 252 can be a standardized connector to which various types and configurations of VADs are connected.

In the case where an axial flow VAD that assists the left ventricle is connected to the blood pump communication module 204 through the universal driveline connector 252, the driving voltages supplied to the three left phase leads 245a, b, c are supplied to the connected axial flow VAD in order to energize coils within the connected axial flow VAD. When the coils within the connected axial flow VAD are energized with the proper driving voltages, a motor within the axial flow VAD is driven at a desired rate.

The blood pump communication module 204 further includes a back electromotive force (BEMF) detector 254 connected to both the LVAD microcontroller 230 and the three left phase leads 245a, b, c. The BEMF detector 254 detects a position of the motor within the connected axial flow VAD through monitoring the electromotive forces fed back from the motor within the axial flow VAD. The BEMF detector 254 outputs information related to the position of the motor within the connected axial flow VAD to the LVAD microcontroller 230. The LVAD microcontroller 230 utilizes the information related to the position of the motor to more accurately control the high FET driver 236 and low FET driver 238. More specifically, a timer set to reflect the current blood pump speed is utilized to precisely sample the BEMF signal for the presence of a zero crossing state. When a zero crossing is detected, the high and low FET drivers for the currently active motor phase are deactivated and the drivers for the FET pair associated with the next sequential phase are activated.

The RVAD microcontroller 232 operates in a manner similar to the LVAD microcontroller 230. In particular, the RVAD microcontroller 232 is connected to a high field effect transistor (FET) driver 256 and a low FET driver 258. The high FET driver 256 and low FET driver 258 are connected to multiple FETs 260-270. Based in part on the control outputs from the microcontroller 206, the RVAD microcontroller 232 controls the high FET driver 256 and low FET driver 258 to supply control voltages to FETs 260-270. In this manner, the FETs 260-270 act as switches for alternately supplying a driving voltage and a ground to each of three right phases leads 265a, b, c. The three right phase leads 265a, b, c are connected through the universal driveline connector 252 to, for example, an axial flow VAD.

In the case where an axial flow VAD configured to assist the right ventricle is connected to the blood pump communication module 204 through the universal driveline connector 252, the driving voltages supplied to the three right phase leads 265a, b, c are also supplied to the connected axial flow VAD in order to energize coils within the connected axial flow VAD. When the coils within the connected axial flow VAD are energized with the proper driving voltages, a motor within the axial flow VAD is driven at a desired rate.

The blood pump communication module 204 further includes a back electromotive force (BEMF) detector 272 connected to both the RVAD microcontroller 232 and the three right phase leads 265a, b, c. The BEMF detector 272 detects a position of the motor within the connected axial flow VAD by monitoring the electromotive forces fed back from the motor within the axial flow VAD. The BEMF detector 272 outputs information related to the position of the motor within the connected axial flow VAD to the RVAD microcontroller 232. The RVAD microcontroller 232 utilizes the information related to the position of the motor to more accurately control the high FET driver 256 and low FET driver 258. More specifically, a timer set to reflect the current blood pump speed is utilized to precisely sample the BEMF signal for the presence of a zero crossing state. When a zero crossing is detected, the high and low FET drivers for the currently active motor phase are deactivated and the drivers for the FET pair associated with the next sequential phase are activated.

The blood pump communication module 204 further includes a lead integrity monitor 274 connected between the three left phase leads 245a, b, c and the three right phase leads 265a, b, c. The lead integrity monitor 274 monitors the status of the three left phase leads 245a, b, c and the three right phase leads 265a, b, c to determine if any of the phase leads or their backups (not shown) are damaged or broken. In the case that the lead integrity monitor 274 determines that one or more of the phase leads is damaged or broken, the lead integrity monitor 274 notifies the corresponding VAD microcontroller 230 or 232 and the microcontroller 206. Consequently, after the microcontroller 206 detects the broken or damaged wire in a circuit, the microcontroller 206 alerts and notifies the user patient of the damaged or broken lead. Furthermore, the microcontroller 206 outputs a repair notice to one or more of the system display module 208 and the status symbols 210 so that the blood pump controller 202 displays to a user a notice that the blood pump communication module 204 needs attention or should be repaired. Alternatively or additionally, the microcontroller 206 outputs a repair notice to one or more of the wireless communication module 214 and the wired communication module 216 such that an external medical monitor can be notified that the blood pump communication module 204 needs attention or should be repaired.

The blood pump communication module 204 further includes a backup drive controller 276 connected to the communication interface 234, LVAD microcontroller 230, RVAD microcontroller 232, high FET driver 236, low FET driver 238, BEMF detector 254, high FET driver 256, low FET driver 258, and BEMF detector 272. The communication interface 234 relays the control outputs from the microcontroller 206 to the backup drive controller 276. The backup drive controller 276 monitors the operating status of both the LVAD microcontroller 230 and RVAD microcontroller 232. If the backup drive controller 276 determines that either the LVAD microcontroller 230 or the RVAD microcontroller 232 is failing to operate properly, the backup drive controller 276 can takeover operations for the failing microcontroller. In this manner, the backup drive controller 276 ensures seamless operation of the blood pump communication module 204, and consequently any connected axial flow VADs, even in the case of a fault.

The blood pump communication module 204 further includes a power conditioning and monitoring module 278 that is connected to the power system of the blood pump controller 202 through the common signal interface 224. The power conditioning and monitoring module 278 converts the power received from the blood pump controller 202 into, among other things, a first power signal intended to drive the logic-based circuitry included in the blood pump communication module 204 and a second power signal intended to drive any axial flow VADs connected to the blood pump communication module 204.

FIG. 3 depicts an alternate example in which a blood pump controller 302 is connected to a blood pump communication module 304 that supports one or more blood pumps 106, 108, such as one or more centrifugal flow VADs. The blood pump controller 302 includes similar components to the blood pump controller 202 and operates in a manner similar to those described above with respect to FIGS. 2A, 2B. Therefore, a detailed description of the blood pump controller 302 will be omitted for the sake of brevity.

The blood pump communication module 304 includes a LVAD communication interface 330 and a RVAD communication interface 332. Based on the commands produced by the microcontroller 306 of the blood pump controller 302 for operating the blood pump communication module 304, the LVAD communication interface 330 outputs signals necessary to operate a centrifugal flow VAD configured to assist the left ventricle. Likewise, based on the commands produced by the microcontroller 306 for operating the blood pump communication module 304, the RVAD communication interface 332 outputs signals necessary to operate a centrifugal flow VAD configured to assist the right ventricle.

The blood pump communication module 304 further includes a power conditioning and monitoring module 378 that is connected to the power system of the blood pump controller 302 through the common signal interface 324. The power conditioning and monitoring module 378 converts the power received from the blood pump controller 302 into, among other things, a first power signal intended to drive the logic-based circuitry included in the blood pump communication module 304, such as the LVAD communication interface 330 and the RVAD communication interface 332, and a second power signal intended to drive any centrifugal flow VADs connected to the blood pump communication module 304.

Output leads of the LVAD communication interface 330, the RVAD communication interface 332, and the power conditioning and monitoring module 378 connect to one or more centrifugal flow VADs through a universal driveline connector 352. The universal driveline connector 352 can be a standardized connector to which various types and configurations of VADs are connected.

The blood pump communication module 304 further includes a lead integrity monitor 374 connected between the universal driveline connector 352 and the LVAD communication interface 330, the power conditioning and monitoring module 378, and the RVAD communication interface 332. The lead integrity monitor 374 monitors the status of the output leads of the LVAD communication interface 330, the RVAD communication interface 332, and the power conditioning and monitoring module 378 to determine if any of the phase leads or their backups (not shown) are damaged or broken. In the case that the lead integrity monitor 374 determines that one or more of the output leads is damaged or broken, the lead integrity monitor 374 notifies the corresponding VAD communication interface 330 or 332 and the microcontroller 306. As a result of notification, the LVAD communication interface 330 or the RVAD communication interface 332 adjusts its control outputs as necessary to continue proper and uninterrupted operation of any connected centrifugal flow VADs. Furthermore, the microcontroller 306 outputs a repair notice to one or more of the system display module 308 and the status symbols 310 such that the blood pump controller 302 can display to a user a notice that the blood pump communication module 304 needs attention or should be repaired. Alternatively or additionally, the microcontroller 306 outputs a repair notice to one or more of the wireless communication module 314 and the wired communication module 316 such that the an external medical monitor can be notified that the blood pump communication module 304 needs attention or should be repaired.

Figure 4A:
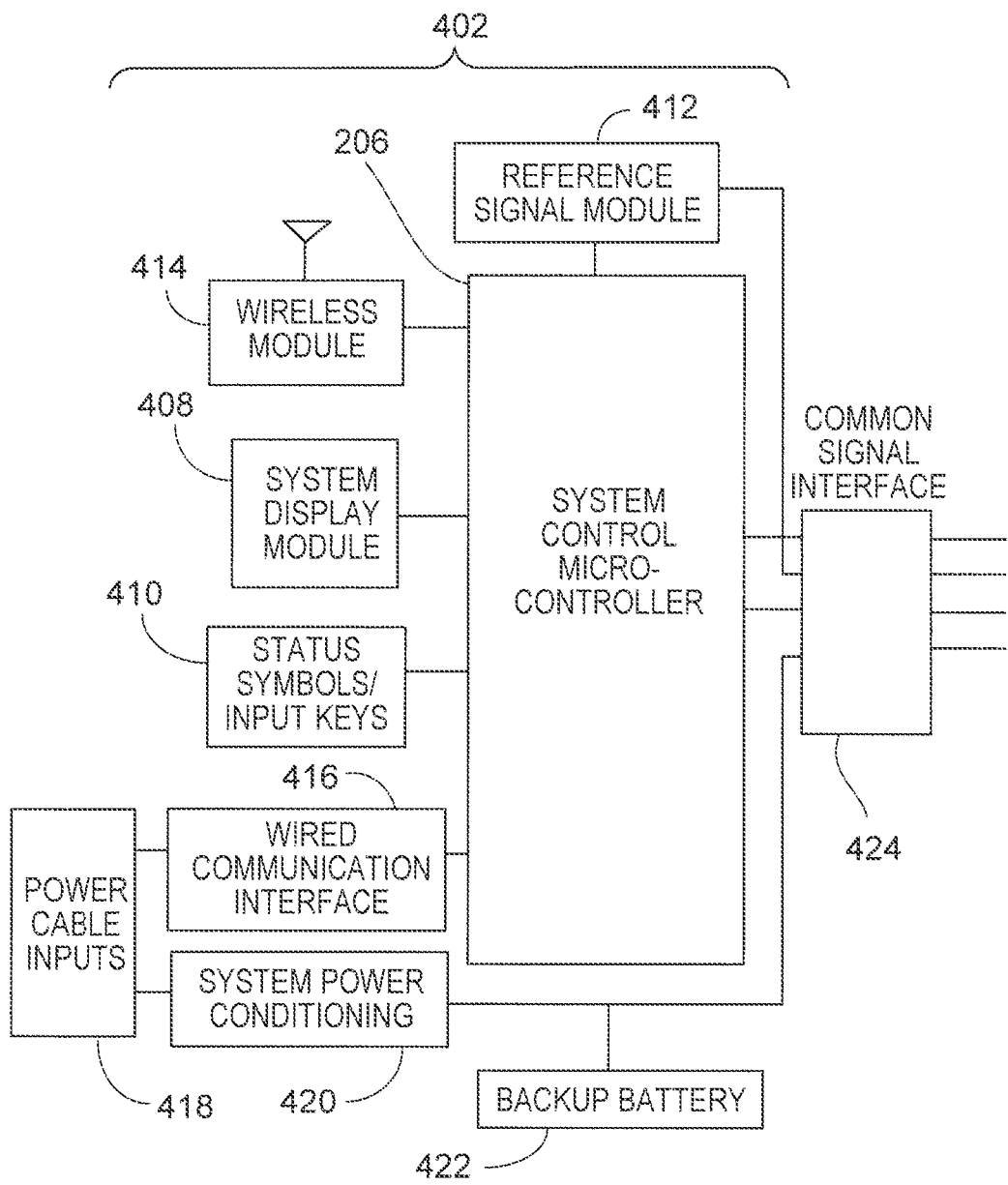
FIGS. 4A-4B are schematic representations of a universal rotary blood pump controller and a rotary blood pump communication module configured to communicate with an axial flow rotary blood pump and a centrifugal flow rotary blood pump.
Figure 4B:
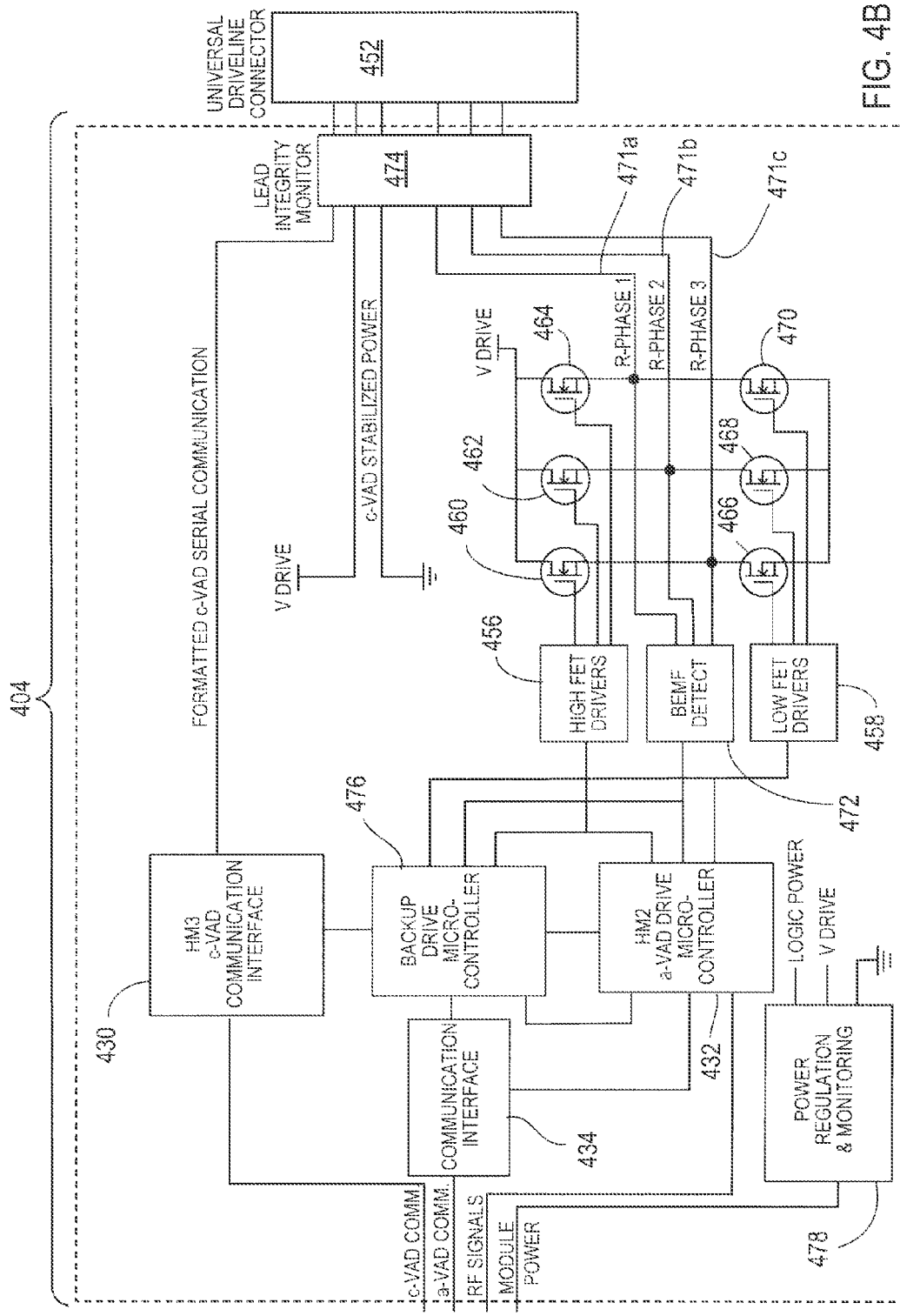

FIGS. 4A, 4B depict an alternate example in which a blood pump controller 402 connected to a blood pump communication module 404 configured to support one or more blood pumps 106, 108, such as a centrifugal flow VAD and an axial flow VAD. The blood pump controller 402 includes similar components to the blood pump controller 202 and operates in a manner similar to those described above with respect to the blood pump controller 202 of FIGS. 2A and 2B. Therefore, a detailed description of the blood pump controller 402 will be omitted for the sake of brevity.

The blood pump communication module 404 includes a VAD communication interface 430 and a VAD microcontroller 432. Based on the commands produced by the microcontroller 406 of the blood pump controller 402 for operating the blood pump communication module 404, the VAD communication interface 430 outputs signals necessary to operate a centrifugal flow VAD. Likewise, based on the commands produced by the microcontroller 406 for operating the blood pump communication module 404, the VAD microcontroller 432 generates and outputs signals necessary to operate an axial flow VAD.

The blood pump communication module 404 further includes a power conditioning and monitoring module 478 that is connected to the power system of the blood pump controller 402 through the common signal interface 424. The power conditioning and monitoring module 478 converts the power received from the blood pump controller 402 into, among other things, a first power signal intended to drive the logic-based circuitry included in the blood pump communication module 404 and a second power signal intended to drive any VADs connected to the blood pump communication module 404.

The VAD microcontroller 432 is connected to a high field effect transistor (FET) driver 456 and a low FET driver 458. The high FET driver 456 and low FET driver 458 are connected to multiple FETs 460-470. Based in part on the control outputs from the microcontroller 406, the VAD microcontroller 432 controls the high FET driver 456 and low FET driver 458 to supply control voltages to FETs 460-470. In this manner, the FETs 460-470 act as switches for alternately supplying a driving voltage and a ground to each of three phases leads 471$a$, $b$, $c$. The three phase leads 471$a$, $b$, $c$ are connected through a universal driveline connector 452 to an axial flow VAD.

In the case where an axial flow VAD is connected to the blood pump communication module 404 through the universal driveline connector 452, the driving voltages supplied to the three phase leads 471$a$, $b$, $c$ are also supplied to the connected axial flow VAD in order to energize coils within the connected axial flow VAD. When the coils within the connected axial flow VAD are energized with the proper driving voltages, a motor within the axial flow VAD is driven at a desired rate.

The blood pump communication module 404 further includes a back electromotive force (BEMF) detector 472 connected to both the VAD microcontroller 432 and the three phase leads 471a, b, c. The BEMF detector 472 detects a position of the motor within the connected axial flow VAD by monitoring the electromotive forces fed back from the motor within the axial flow VAD. The BEMF detector 472 outputs information related to the position of the motor within the connected axial flow VAD to the VAD microcontroller 432. The VAD microcontroller 432 utilizes the information related to the position of the motor to more accurately control the high FET driver 456 and low FET driver 458. More specifically, a timer set to reflect the current blood pump speed is utilized to precisely sample the BEMF signal for the presence of a zero crossing state. When a zero crossing is detected, the high and low FET drivers for the currently active motor phase are deactivated and the drivers for the FET pair associated with the next sequential phase are activated.

The blood pump communication module 404 further includes a backup drive controller 476 connected to VAD microcontroller 432, high FET driver 456, low FET driver 458, and BEMF detector 472. A communication interface 434 relays the control outputs from the microcontroller 406 to both of the VAD microcontroller 432 and the backup drive controller 476. The backup drive controller 476 monitors the operating status of both the VAD microcontroller 432. If backup drive controller 476 determines that either the VAD microcontroller 432 is failing to operate properly, the backup drive controller 476 takes over operations for VAD microcontroller 432. In this manner, the backup drive controller 476 ensures seamless operation of the blood pump communication module 404, and consequently any connected axial flow VADs in the case of a fault.

The blood pump controllers 202, 302, and 402 as described above with regard to FIGS. 2-4 can be interchangeable with one another or can be the same blood pump controller. In other words, a single blood pump controller can be connected to any of varying blood pump communication modules 204, 304, or 404 and effectively control the blood pump communication module. Such interchangeability provides for modularity in the blood pump controller and the blood pump communication module and creates a more efficient design. For example, a health care provider can separately purchase a varying number of blood pump controllers and blood pump communication modules to meet its needs. Furthermore, a common blood pump controller decreases manufacturing costs for the system as a whole.

Figure 5:
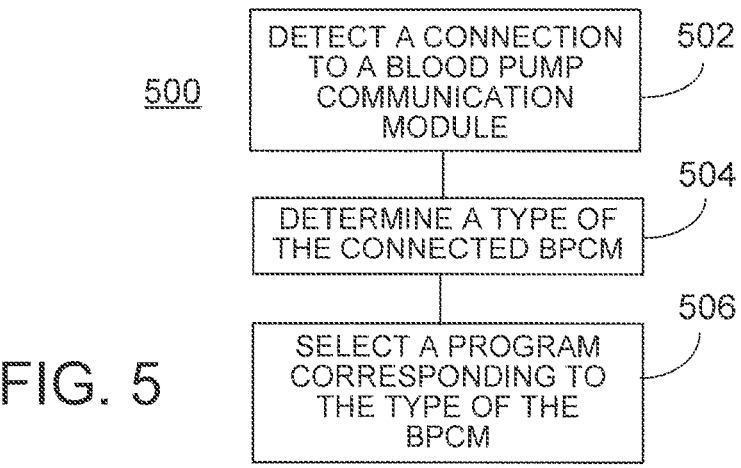
FIG. 5 is a flow chart illustrating a process by which a blood pump controller determines a set of control logic for operating one or more blood pumps.

In use, in order to provide the blood pump communication modules with the proper control commands, each of the blood pump controllers described above determine the type of blood pump communication module to which it is connected. FIG. 5 illustrates an exemplary process 500 by which a blood pump controller determines a set of control logic used to operate a blood pump communication module to which it is connected.

Referring to FIG. 5, the blood pump controller determines that a blood pump communication module has been connected (502). The blood pump controller can make this determination in a number of ways. For example, the blood pump controller can periodically send polling signals to the common signal interface. When a blood pump communication device is connected to the blood pump controller, the blood pump communication device receives the polling signals and responds with a predetermined response. Upon receiving the response, the blood pump controller determines that a blood pump communication module has been connected to the blood pump controller. Alternatively, the blood pump controller can employ hardware or software based interrupt routines to determine that a blood pump communication module has been connected. Upon being connected to the blood pump controller, a blood pump communication module triggers an interrupt state in the blood pump controller that results in a determination, by the blood pump controller, that a blood pump communication module has been connected. Alternatively, the blood pump controller can determine that a blood pump communication module has been connected by detecting a change in the resistive characteristics at the common signal interface. Alternatively, the blood pump controller can determine that a blood pump communication module has been connected by detecting a change in the voltage level on the common signal interface.

The blood pump controller determines the type of blood pump communication module to which the blood pump controller is connected (504). The blood pump controller can make this determination in a number of ways. For example, where a blood pump controller polls the communication signal interface to determine if a blood pump communication module has been connected, the blood pump controller determines the type of blood pump communication module connected based on at least one of the format and the content of the response received from a connected blood pump communication module. Alternatively, where a blood pump controller determines that a blood pump communication module has been connected by detecting a change in the resistive characteristics at the common signal interface, the blood pump controller determines the type of blood pump communication module based on the detected resistance at the common signal interface. Alternatively, where a blood pump controller determines that a blood pump communication module has been connected by detecting a change in the voltage level on the common signal interface, the blood pump controller determines the type of blood pump communication module based on the detected voltage at the common signal interface.

The blood pump controller determines and selects one of various instruction sets corresponding to the type of blood pump communication module to which the blood pump controller is connected (506). For example, the blood pump controller can select the appropriate control program by comparing the response from the connected communication module to a table of expected responses for each type of blood pump controller. The control programs can be based on any one of a combination of pulsatility index, continuous flow, or (artificial) pulse. The blood pump controller can then execute the chosen instruction set to control the blood pump communication module. Optionally, more than one control program can be chosen where each control program can operate at different time or duration.

As the blood pump controller can be connected to various types blood pump communication modules, the universal driveline connector 252, 252, 452 allows various types of VADs to be connected to any given blood pump communication module. However, unlike the blood pump controller, each type of blood pump communication module controls a certain type of connected VAD. In fact, a blood pump communication module that attempts to drive a VAD that is not supported by or is improperly connected to the blood pump communication module may damage the VAD. In the case where the VAD has already been implanted in a patient, damaging the VAD could cause great harm.

Figure 6:
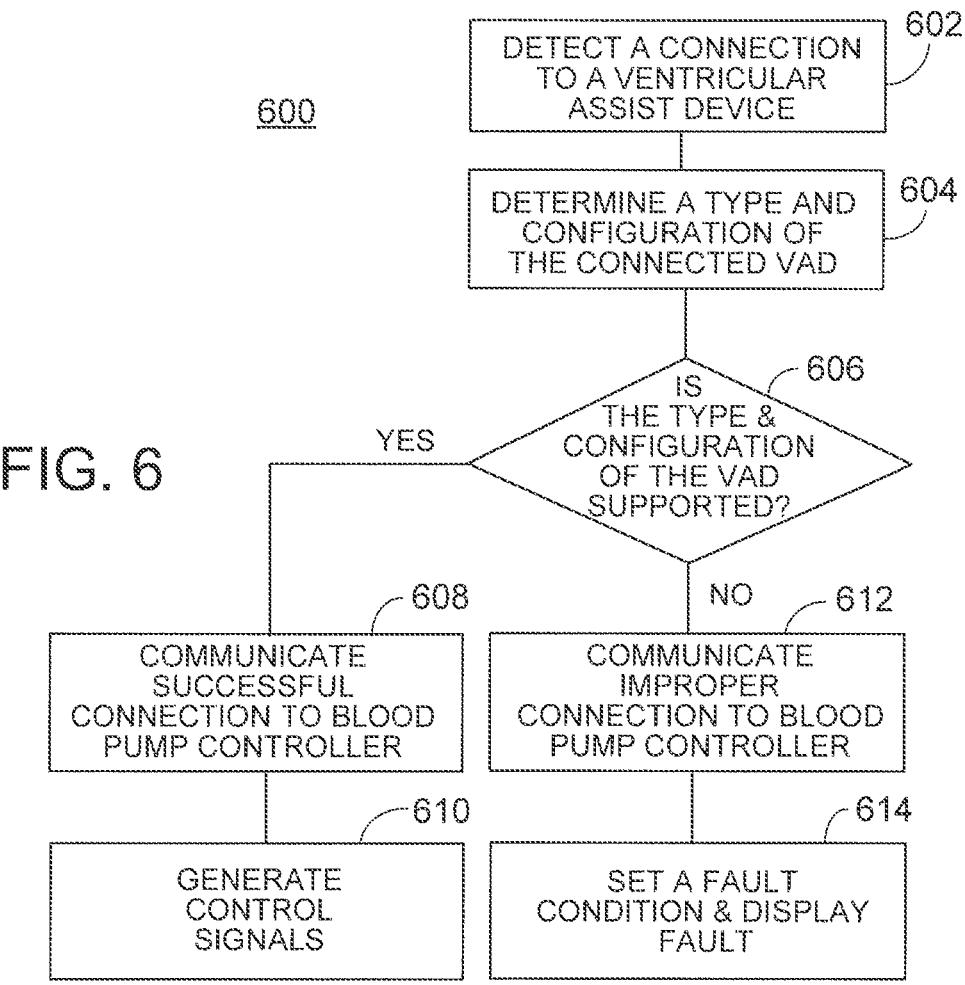
FIG. 6 is a flow chart illustrating a process by which a blood pump controller and a blood pump communication module determine and handle supportability of a connected blood pump.

FIG. 6 illustrates a process 600 by which a blood pump controller and a blood pump communication module determine and handle supportability of a connected VAD. The blood pump communication module determines that a VAD has been connected (602). The blood pump communication module makes this determination in a number of ways. For example, the blood pump communication module can periodically send polling signals to the universal driveline connector. When a VAD is connected to the blood pump communication module, the VAD receives the polling signals and responds with a predetermined response. Upon receiving the response, the blood pump communication module can determine that a VAD has been connected to the blood pump communication module. Alternatively, the blood pump communication module can employ hardware or software based interrupt routines to determine that a VAD has been connected. Upon being connected to the blood pump communication module, a VAD can trigger an interrupt state in the blood pump communication module that results in a determination, by the blood pump communication module, that a VAD has been connected. Alternatively, the blood pump communication module can determine that a VAD has been connected by detecting a change in the resistive characteristics at the universal driveline connector.

The blood pump communication module determines the type of VAD to which the blood pump communication module is connected (604). The blood pump communication module makes this determination in a number of ways. For example, where a blood pump communication module polls the universal driveline connector to determine if a VAD has been connected, the blood pump communication module can determine the type of VAD connected based on at least one of the format and the content of the response received from a connected VAD. Alternatively, where a blood pump communication module determines that a VAD has been connected by detecting a change in the resistive characteristics at the universal driveline connector, the blood pump communication module can determine the type of VAD based on the detected resistance at the universal driveline connector.

The blood pump communication module determines whether it is capable of supporting the type of VAD to which the blood pump communication module is connected and the manner in which it is connected (606). If the blood pump communication module determines that it is capable of supporting the connected VAD, the blood pump communication module notifies the blood pump controller that a successful connection has been made (608). Based on receiving a notification that a VAD has been successfully connected to the blood pump communication module, the blood pump controller begins generating control commands that the blood pump communication module uses to drive the VAD (610).

If the blood pump communication module determines that it is not capable of supporting the connected VAD, the blood pump communication module notifies the blood pump controller that an improper connection has been made (612). Based on receiving a notification that a VAD has been improperly connected to the blood pump communication module, the blood pump controller takes the necessary action to notify the user of the improper connection. For example, the blood pump controller can output an improper connection notice to one or more of the system display module and the status symbols such that the blood pump controller displays to a user a notice that an improper connection has been made. Alternatively, or additionally, the blood pump communication module can output an improper connection notice to one or more of the wireless communication module and the wired communication module such that an external medical monitor can be notified that the blood pump communication module should be repaired. Furthermore, based on receiving a notification that a VAD has been improperly connected to the blood pump communication module, the blood pump controller will not send control commands to the blood pump communication module so that the blood pump communication module does attempt to drive the improperly connected VAD. As such, the blood pump controller will avoid damaging an improperly connected VAD.

A number of examples have been described. Nevertheless, it will be understood that various modifications may be made without departing from the spirit and scope of the disclosure. For example, while the blood pump communication module may be connected to one or more blood pumps via a cable, as described above with regard to FIG. 1, the blood pump communication module may be connected to the one or more blood pumps via a wireless connection. Accordingly, other implementations are within the scope of the following claims.

What is claimed is:

1. An external control system for use with an implantable blood pump, the system comprising:
   a microcontroller;
   a communication module coupled to the microcontroller and configured to operate the implantable blood pump;
   a rechargeable battery coupled to the microcontroller and configured to power the microcontroller, the communication module, and the implantable blood pump; and
   a system power conditioning module coupled to the microcontroller and configured to condition power from an external power source for charging the battery.

2. The external control system of claim 1, wherein the external power source is a wall outlet.

3. The external control system of claim 1, wherein the system power conditioning module is further configured to condition power to drive the communication module and the implantable blood pump.

4. An external control system for use with an implantable blood pump, the system comprising:
   a microcontroller;
   a communication module coupled to the microcontroller and configured to operate the implantable blood pump, the communication module comprising:
      a backup drive controller; and
      a communication interface configured to relay control inputs from the microcontroller to the backup drive controller, wherein the backup drive controller is configured to take over operation from the microcontroller to operate the implantable blood pump if the microcontroller fails to operate properly;
   a rechargeable battery coupled to the microcontroller and configured to power the microcontroller, the communication module, and the implantable blood pump; and
   a system power conditioning module coupled to the microcontroller and configured to condition power from an external power source for charging the battery.

5. The external control system of claim 1, wherein the microcontroller, communication module, and battery are included in a blood pump controller assembly, wherein the communication module is formed as a PC card for insertion into the controller assembly or as a daughterboard or mezzanine board in the controller assembly.

6. The external control system of claim 1, wherein the communication module further comprises a back electromotive force detector configured to detect a position of a motor of the implantable blood pump based on a signal of electromotive forces fed back by the motor and to output information related to position of the motor to the microcontroller and wherein the microcontroller is configured to modify control outputs to the communication module based on the output information.

7. The external control system of claim 6, further comprising a timer set to reflect a current blood pump speed, wherein the electromotive force detector is configured to sample the signal of electromotive forces corresponding to a presence of a zero crossing state.

8. The external control system of claim 1, wherein the microcontroller is configured to detect if a fault is present in one or more components of the external control system and to alter an output to the communication module or terminate output to the communication module when the fault is detected.

9. The external control system of claim 1, further comprising a visual indicator to provide a status of the implantable blood pump, a power level of the battery, or a fault status of one or more components of the external control system.

10. The external control system of claim 1, further comprising a communication interface configured to transmit information to an external medical monitor or controller display.

11. The external control system of claim 1, wherein the microcontroller is configured to determine a type of the communication module and select a control mode based on the type of the communication module, wherein the control mode comprises at least one of a pulsatility index, continuous flow, and artificial pulse.

12. The external control system of claim 11, wherein the microcontroller is configured to send a polling signal to the communication module via a communication interface and determine the type of the communication module based on a response to the polling signal sent by the communication module.

13. The external control system of claim 11, wherein the microcontroller is configured to detect a change in resistive characteristics at a communication interface and determine the type of the communication module based on the detected change in resistive characteristics.

14. The external control system of claim 11, wherein the microcontroller is configured to detect a change in a voltage level at a communication interface and determine the type of communication module based on the detected change in the voltage level.

15. The external control system of claim 1, wherein the communication module further comprises a lead integrity monitor configured to determine if one or more leads connected to the implantable blood pump are damaged, wherein the lead integrity monitor is further configured to provide an indication of a damaged lead to the microcontroller.

16. The external control system of claim 15, wherein the microcontroller is configured to alert a user when the lead integrity monitor provides the indication of a damaged lead.

17. The external control system of claim 15, wherein the microcontroller is configured to output a repair notice to an external monitor when the lead integrity monitor provides the indication of a damaged lead.

18. The external control system of claim 1, further comprising a reference signal module coupled to the microcontroller, wherein the reference signal module is configured to supply one or more reference signals to the microcontroller for comparison with signals output by components of the external control system.

19. The external control system of claim 1, further comprising a reference signal module coupled to the microcontroller, wherein the reference signal module is configured to compare one or more reference signals with signals output by components of the external control system and output the results of the comparison to the microcontroller.

* * * * *